(12) United States Patent
Shluzas

(10) Patent No.: US 6,554,832 B2
(45) Date of Patent: Apr. 29, 2003

(54) POLYAXIAL TRANSVERSE CONNECTOR

(75) Inventor: Alan E. Shluzas, Millis, MA (US)

(73) Assignee: Endius Incorporated, Plainville, MA (US)

( * ) Notice: Subject to any disclaimer, the term of this patent is extended or adjusted under 35 U.S.C. 154(b) by 69 days.

(21) Appl. No.: 09/824,411

(22) Filed: Apr. 2, 2001

(65) Prior Publication Data

US 2002/0143330 A1 Oct. 3, 2002

(51) Int. Cl.$^7$ ................................................ A61B 17/70
(52) U.S. Cl. ........................................... 606/61; 606/72
(58) Field of Search .......................... 606/59, 61, 60, 606/54, 63, 64, 72

(56) References Cited

U.S. PATENT DOCUMENTS

| | | | |
|---|---|---|---|
| 5,176,680 A | 1/1993 | Vignaud et al. | 606/61 |
| 5,569,246 A | * 10/1996 | Ojima et al. | 606/61 |
| 5,609,592 A | * 3/1997 | Brumfield et al. | 606/61 |
| 5,910,142 A | 6/1999 | Tatar | 606/61 |
| 5,980,523 A | 11/1999 | Jackson | 606/61 |
| 6,083,226 A | 7/2000 | Fiz | 606/61 |
| 6,096,039 A | 8/2000 | Stoltenberg et al. | |
| 6,179,838 B1 | * 1/2001 | Fiz | 606/61 |
| 6,238,396 B1 | 5/2001 | Lombardo | 606/61 |

OTHER PUBLICATIONS

An advertisement for a crosslink from "Spine" vol. 26, No. 4, dated Feb. 15, 2001.

* cited by examiner

Primary Examiner—Cary E. O'Connor
(74) Attorney, Agent, or Firm—Tarolli, Sundheim, Covell & Tummino L.L.P.

(57) ABSTRACT

A transverse connector (10) for interconnecting first and second spine rods (12) extending along a spinal column includes a first connecting member (30) connectable with the first spine rod (12). A second connecting member (44) is connectable with the second spine rod (12). A connecting rod (42) connected to the first and second connecting members (30, 44) extends between the first and second connecting members. The connecting rod (42) is rotatable about a longitudinal axis (51) of said connecting rod relative to said first connecting member and pivotable about a pivot axis (54) extending transverse to said longitudinal axis. A fastener (58) connects the connecting rod (42) to the first connecting member (30) in any one of a plurality of positions about the longitudinal axis of the connecting rod and in any one of a plurality of pivot positions about the pivot axis. The connecting rod (42) is also positionable along the longitudinal axis (51) of the connecting rod relative to the first connecting member (30).

17 Claims, 2 Drawing Sheets

US 6,554,832 B2

POLYAXIAL TRANSVERSE CONNECTOR

TECHNICAL FIELD

The present invention relates to a transverse connector for interconnecting spine rods that retain vertebrae of a spinal column in a desired spatial relationship.

BACKGROUND OF THE INVENTION

A known transverse connector for interconnecting spine rods extending along a spinal column is disclosed in U.S. Pat. No. 6,096,039. U.S. Pat. No. 6,096,039 discloses a transverse connector including connecting members for connecting the transverse connector to the spine rods. A transverse bar is connected to the connecting members. One of the connecting members pivots about a pivot axis relative to the transverse bar.

SUMMARY OF THE INVENTION

The present invention relates to a transverse connector for interconnecting first and second spine rods extending along a spinal column. The transverse connector includes a first connecting member connectable with the first spine rod. A second connecting member is connectable with the second spine rod. A connecting rod connected to the first and second connecting members extends between the first and second connecting members.

The connecting rod is rotatable about a longitudinal axis of the connecting rod relative to the first connecting member and pivotable about a pivot axis extending transverse to the longitudinal axis. A fastener connects the connecting rod to the first connecting member in any one of a plurality of positions about the longitudinal axis of the connecting rod and in any one of a plurality of pivot positions about the pivot axis. The connecting rod is also positionable along the longitudinal axis of the connecting rod relative to the first connecting member.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DESCRIPTION OF THE INVENTION

Figure 1:
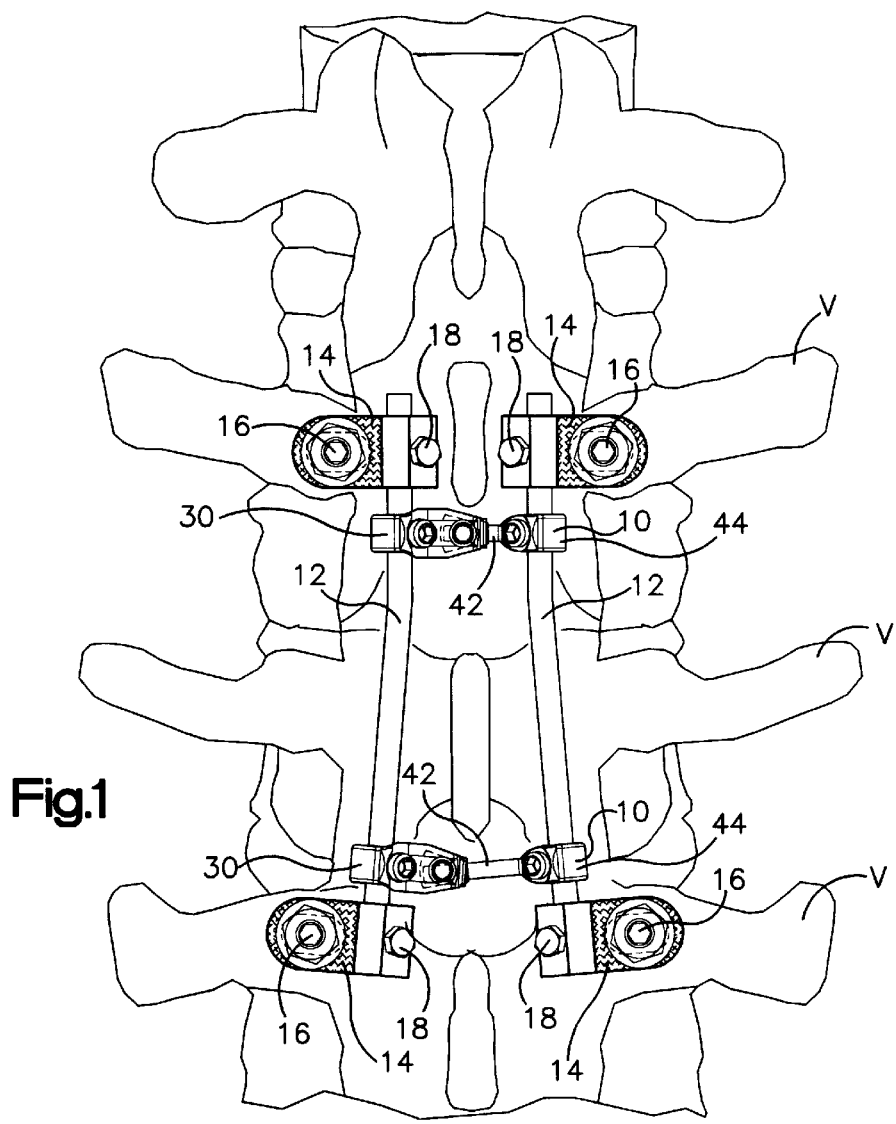
FIG. 1 is an enlarged plan view of transverse connectors of the present invention interconnecting a pair of spine rods which are connected to a spinal column.
Figure 2:
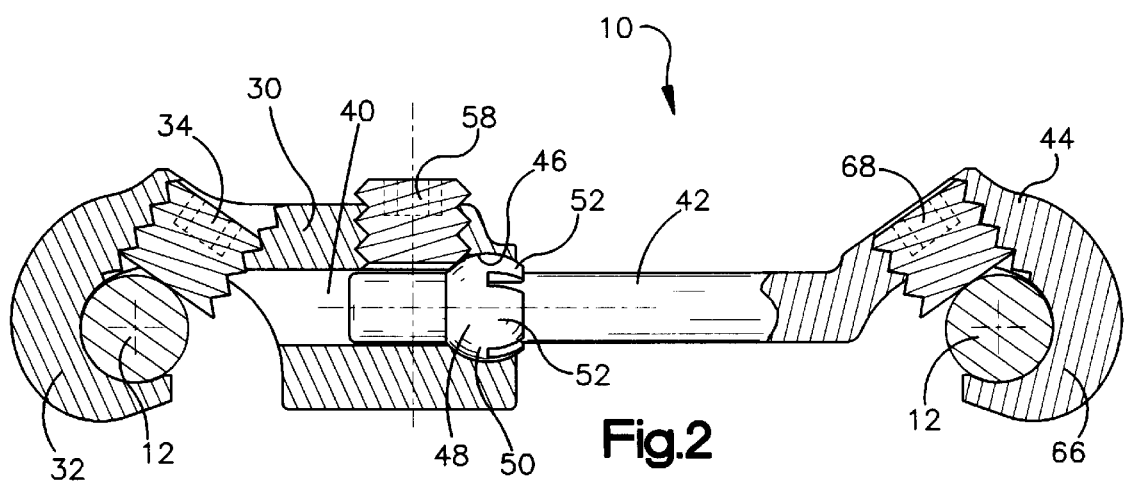
FIG. 2 is a cross-sectional view of the transverse connector in FIG. 1.
Figure 3:
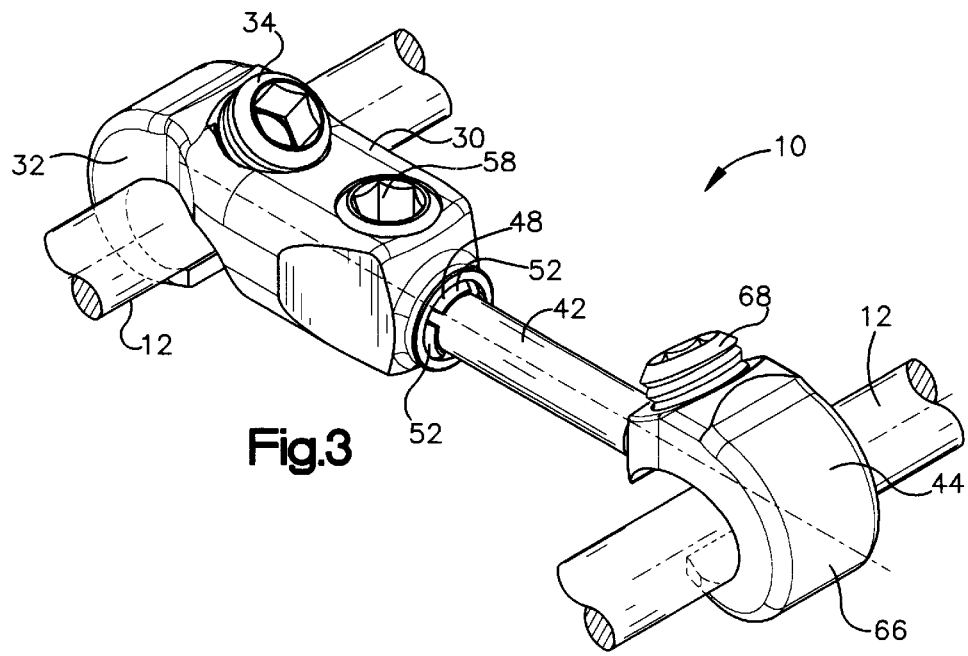
FIG. 3 is a perspective view of the transverse connector in FIG. 1.
Figure 4:
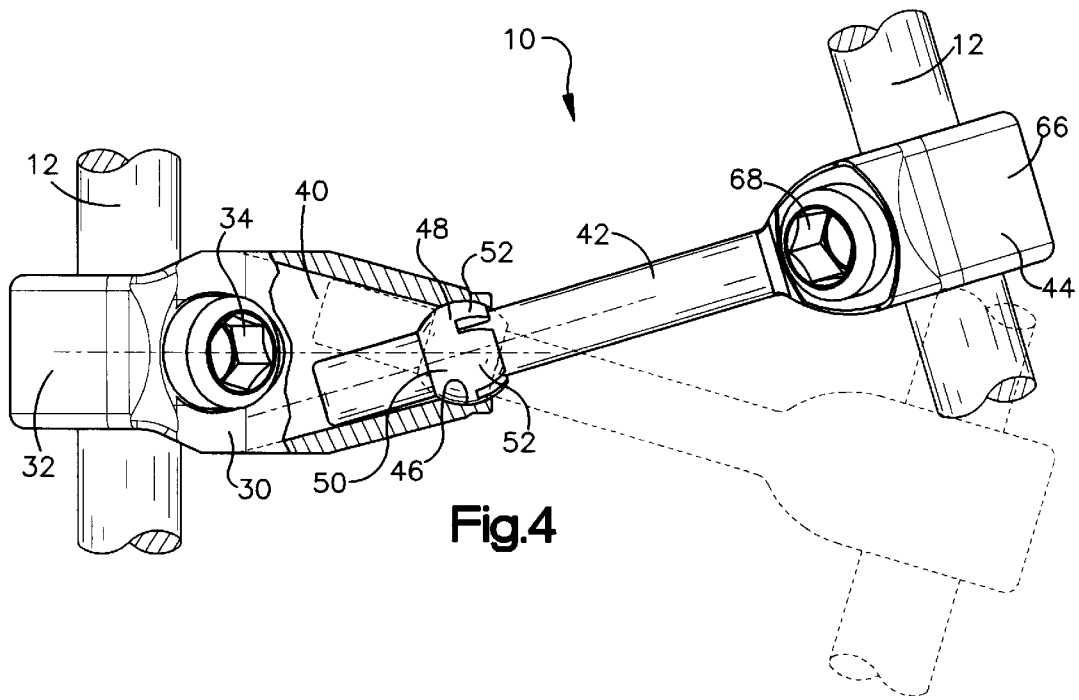
FIG. 4 is an enlarged plan view of the transverse connector of FIG. 1 with portions cut away to show how a connecting rod of the transverse connector is pivoted relative to a connecting member.

A transverse connector 10 constructed in accordance with the present invention is illustrated in FIGS. 1–4. A pair of longitudinal spine rods 12 are connected to vertebrae V of a spinal column to maintain relative positions of the vertebrae. It will be apparent that the rods 12 may be located anywhere along the spinal column and the location of the rods illustrated in FIG. 1 is for example purposes.

Each of the rods 12 (FIG. 1) is elongate and has a sufficient length to span at least two vertebrae V. A plurality of connectors 14 and fasteners 16 connect the rods 12 with the vertebrae V. The connectors 14 and the fasteners 16 may be of any known construction. The connectors 14 include openings through which the fasteners 16 extend to connect the connectors to the vertebrae V. The connectors 14 include set screws 18 for clamping the longitudinal rods 12 in openings extending through the connectors.

At least one transverse connector 10 interconnects the rods 12. The transverse connector 10 blocks relative movement of the rods 12 so the vertebrae V connected to the rods are maintained in their desired relative positions and do not pivot relative to an anterior/posterior axis or a longitudinal central axis of the spinal column. It will be apparent that the transverse connector 10 may be located anywhere along the rods 12 and that any number of transverse connectors may be used.

The transverse connector 10 (FIGS. 1–4) includes a connecting member 30 connectable with one of the spine rods 12. The connecting member 30 (FIGS. 2 and 3) has a hook portion 32 that extends around a portion of the spine rod 12. A clamping member or set screw 34 threadably engages the connecting member 30 and clamps the spine rod 12 to the hook portion 32.

The connecting member 30 (FIGS. 2 and 4) has an opening 40 that extends through a portion of the connecting member. The opening 40 receives a connecting rod 42 fixedly connected to a second connecting member 44 and extending from the second connecting member 44. The connecting rod 42 is integrally formed with the second connecting member 44. The opening 40 defines a socket 46 for receiving a ball 48 to define a ball joint 50. The connecting rod 42 extends through the ball 48 and into the opening 40 in the connecting member 30. The connecting rod 42 is rotatable about a longitudinal axis 51 of the connecting rod and pivotable about a pivot axis 54 extending transverse to the longitudinal axis. The connecting rod 42 is also slidable relative to the ball 48 along the axis 51 and thus is positionable in any one of a plurality of positions along the longitudinal axis 51 relative to the connecting member 30 and the ball 48.

The ball 48 has four tabs 52 engageable with the connecting rod 42. A set screw 58 (FIGS. 2 and 3) threadably engages the connecting member 30 and clamps the connecting rod 42 against the connecting member 30 to prevent movement of the connecting rod relative to the connecting member. Accordingly, the set screw 58 connects the connecting rod 42 to the connecting member 30 in any one of a plurality of positions about the longitudinal axis 51, in any one of a plurality of pivot positions about the pivot axis 54, and in any one of a plurality of positions along the longitudinal axis 51 of the connecting rod. It is contemplated that the connecting rod 42 could threadably engage the ball 48 to position the connecting rod relative to the ball.

The connecting member 44 (FIGS. 2 and 3) has a hook portion 66. The hook portion 66 extends around a portion of the other spine rod 12. A clamping member or set screw 68 threadably engages the connecting member 44 and clamps the spine rod 12 to the hook portion 66.

When the transverse connector 10 (FIGS. 1–4) is to be connected to the spine rods 12, the connecting rod 42 is placed through the ball 48. The connecting rod 42 is positioned relative to the connecting member 30. Once the connecting members 30 and 44 have been positioned relative to each other and the spine rods 12, the hook portions 32 and 66 are placed around the spine rods 12. The set screws 34, 58, and 68 are tightened to connect the connecting rod 42 to the connecting member 30 and the transverse connector 10 to the spine rods 12.

From the above description of the invention, those skilled in the art will perceive improvements, changes and modifications. Such improvements, changes and modifications within the skill of the art are intended to be covered by the appended claims.

Having described the invention, the following is claimed:

1. A transverse connector for interconnecting first and second spine rods extending along a spinal column, said transverse connector comprising:

a first connecting member connectable with the first spine rod;

a second connecting member connectable with the second spine rod;

a connecting rod connected to said first and second connecting members and extending between said first and second connecting members, said connecting rod being rotatable about a longitudinal axis of said connecting rod relative to said first connecting member and pivotable about a pivot axis extending transverse to said longitudinal axis; and a fastener for connecting said connecting rod to said first connecting member in any one of a plurality of positions about said longitudinal axis of said connecting rod and in any one of a plurality of pivot positions about said pivot axis.

2. A transverse connector as set forth in claim 1 wherein said connecting rod is positionable in any one of a plurality of positions along said longitudinal axis of said connecting rod relative to said first connecting member.

3. A transverse connector as set forth in claim 2 wherein said fastener connects said connecting rod to said first connecting member in any one of said plurality of positions along said longitudinal axis of said connecting rod relative to said first connecting member.

4. A transverse connector as set forth in claim 1 wherein a ball joint connects said connecting rod to said first connecting member, said ball joint including a ball engaging said connecting rod and a socket in said first connecting member receiving said ball.

5. A transverse connector as set forth in claim 4 wherein said connecting rod extends into an opening in said ball of said ball joint and is positionable along said longitudinal axis of said connecting rod relative to said ball.

6. A transverse connector as set forth in claim 5 wherein said fastener connects said connecting rod to said first connecting member in any one of said plurality of positions along said longitudinal axis of said connecting rod relative to said ball.

7. A transverse connector as set forth in claim 6 wherein said fastener engages said ball to connect said connecting rod to said first connecting member in any one of said plurality of positions about said longitudinal axis of said connecting rod, in any one of said plurality of pivot positions, and in any one of said plurality of positions along said longitudinal axis of said connecting rod.

8. A transverse connector as set forth in claim 1 wherein said first connecting member includes a hook portion for extending around a portion of the first spine rod and a clamping member for clamping the first spine rod to said hook portion.

9. A transverse connector as set forth in claim 8 wherein said second connecting member includes a hook portion for extending around a portion of the second spine rod and a clamping member for clamping the second spine rod to said hook portion of said second connecting member.

10. A transverse connector as set forth in claim 1 wherein said connecting rod is integrally formed with said second connecting member.

11. A transverse connector for interconnecting first and second spine rods extending along a spinal column, said transverse connector comprising:

a first connecting member connectable with the first spine rod;

a second connecting member connectable with the second spine rod;

a connecting rod connected to said first and second connecting members and extending between said first and second connecting members, said connecting rod being positionable along a longitudinal axis of said connecting rod relative to said first connecting member and pivotable about a pivot axis extending transverse to said longitudinal axis;

a fastener for connecting said connecting rod to said first connecting member in any one of a plurality of positions along said longitudinal axis of said connecting rod and in any one of a plurality of pivot positions about said pivot axis; and a ball joint connecting said connecting rod to said first connecting member, said ball joint including a ball engaging said connecting rod and a socket in said first connecting member receiving said ball.

12. A transverse connector as set forth in claim 11 wherein said connecting rod extends into an opening in said ball of said ball joint and is rotatable about said longitudinal axis of said connecting rod relative to said ball.

13. A transverse connector as set forth in claim 12 wherein said fastener connects said connecting rod to said first connecting member in any one of a plurality of positions about said longitudinal axis of said connecting rod relative to said ball.

14. A transverse connector as set forth in claim 13 wherein said fastener engages said ball to connect said connecting rod to said first connecting member in any one of said plurality of pivot positions, in any one of said plurality of positions along said longitudinal axis of said connecting rod, and in any one of said plurality of positions about said longitudinal axis.

15. A transverse connector as set forth in claim 11 wherein said first connecting member includes a hook portion for extending around a portion of the first spine rod and a clamping member for clamping the first spine rod to said hook portion.

16. A transverse connector as set forth in claim 15 wherein said second connecting member includes a hook portion for extending around a portion of the second spine rod and a clamping member for clamping the second spine rod to said hook portion of said second connecting member.

17. A transverse connector as set forth in claim 11 wherein said connecting rod is integrally formed with said second connecting member.

\* \* \* \* \*